(12) United States Patent
Duan et al.

(10) Patent No.: US 10,702,132 B2
(45) Date of Patent: Jul. 7, 2020

(54) SYSTEM AND METHOD FOR USING A CAPSULE DEVICE

(71) Applicant: Ankon Medical Technologies (Shanghai) Co., Ltd., Shanghai (CN)

(72) Inventors: Xiaodong Duan, Pleasanton, CA (US); Shaobang Zhang, Hangzhou (CN)

(73) Assignee: Ankon Medical Technologies (Shanghai) Co., LTD., Shanghai (CN)

( * ) Notice: Subject to any disclaimer, the term of this patent is extended or adjusted under 35 U.S.C. 154(b) by 0 days.

(21) Appl. No.: 16/564,845

(22) Filed: Sep. 9, 2019

(65) Prior Publication Data

US 2019/0387960 A1 Dec. 26, 2019

Related U.S. Application Data

(62) Division of application No. 15/274,845, filed on Sep. 23, 2016, now Pat. No. 10,478,048.

(51) Int. Cl.

| | |
|---|---|
| *A61B 1/00* | (2006.01) |
| *A61B 34/00* | (2016.01) |
| *A61B 5/00* | (2006.01) |
| *A61B 5/06* | (2006.01) |
| *A61B 1/04* | (2006.01) |

(52) U.S. Cl.
CPC .......... *A61B 1/00158* (2013.01); *A61B 1/041* (2013.01); *A61B 5/062* (2013.01); *A61B 5/6861* (2013.01); *A61B 34/73* (2016.02); *A61B 2034/732* (2016.02)

(58) Field of Classification Search
CPC ...... A61B 1/00158; A61B 5/062; A61B 34/73
See application file for complete search history.

(56) References Cited

U.S. PATENT DOCUMENTS

| | | | | |
|---|---|---|---|---|
| 2005/0256398 | A1* | 11/2005 | Hastings | A61B 34/73 600/423 |
| 2008/0300458 | A1* | 12/2008 | Kim | A61B 1/00158 600/118 |
| 2013/0267788 | A1* | 10/2013 | Duan | B25J 11/00 600/300 |
| 2013/0303847 | A1* | 11/2013 | Sitti | A61B 1/00158 600/104 |
| 2015/0018614 | A1* | 1/2015 | Duan | A61B 1/00006 600/109 |

FOREIGN PATENT DOCUMENTS

KR 20040108277 A * 12/2004 ............. A61B 1/00

* cited by examiner

*Primary Examiner* — Aaron B Fairchild

(74) *Attorney, Agent, or Firm* — Treasure IP Group, LLC

(57) ABSTRACT

The present invention discloses a method to move a magnetic capsule linearly both horizontally and linearly in a very controllable fashion, wherein the direction of a combined external magnetic field, the force experienced by the magnetic capsule, the movement direction of the capsule and magnetic direction of the magnetic capsule can be all aligned in parallel to each other.

8 Claims, 20 Drawing Sheets

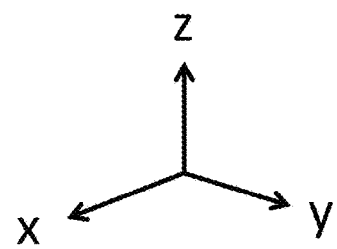
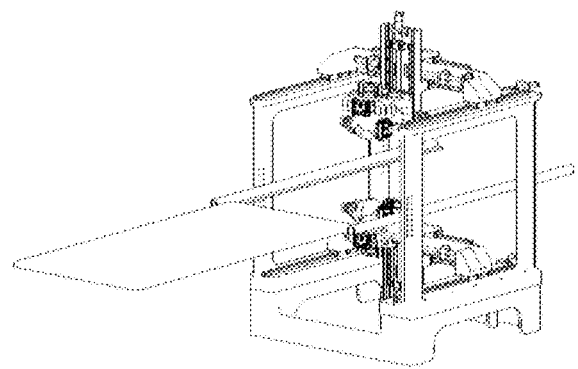
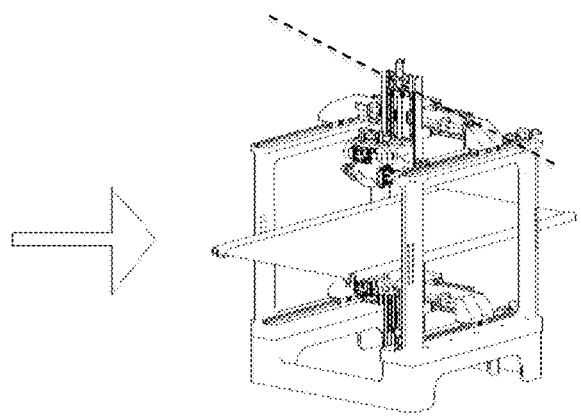
FIG. 2
FIG. 3

FIG. 21  FIG. 22  FIG. 23  FIG. 24
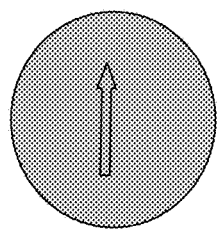 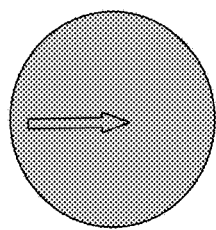 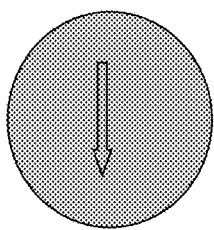 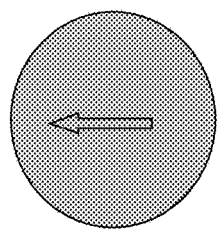
 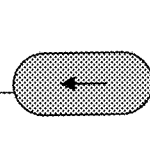  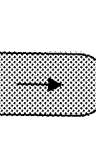
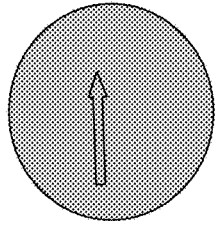 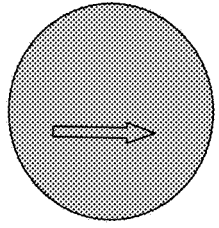 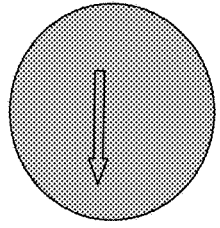 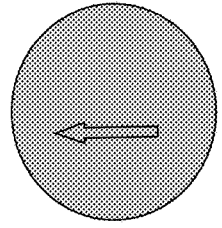

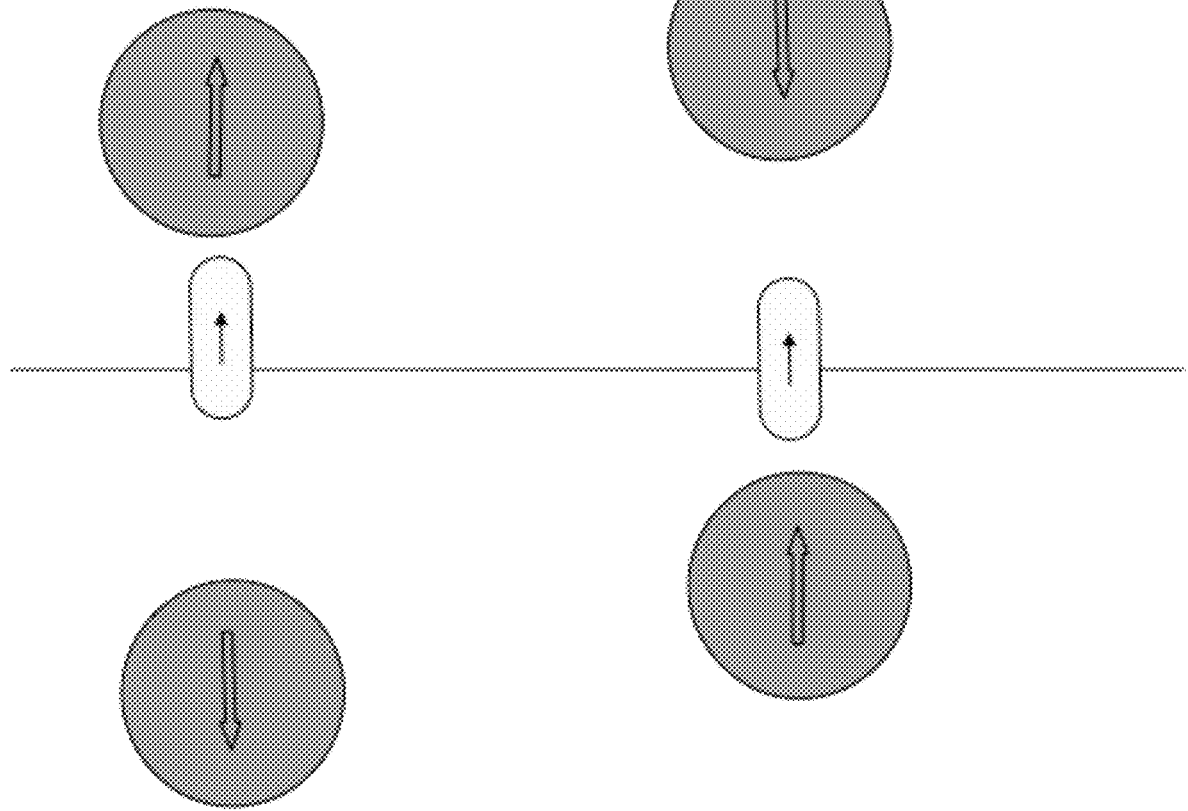

FIG. 29

| | |
|---|---|
| patient lays down the examing bed, the capsule is inside the colon. | move the two magnetic balls directions so that the capsule is imaging the open space (tube hole) of colon. and move the balls to be ahead of the capsule's moving direction. |
| two magnetic balls vertical aligned and have horizontal magnetization. And the distance between the two balls' centers are relatively far (~60cm) | to move the capsule forward rotate the two magnetic balls' magnetization as in Fig.1(a); to move the capsule backward rotate the two magnetic balls' magnetization as in Fig.1(b); |
| moving two magnetic balls together in XY plane to find a relative larger magnetic fields measured by the magnetic sensors inside the capsules | move the two magnetic balls close to each other at the same velocity to near the patient's body surface but not touch the patient for the safe reason. The capsule will move toward the line between the magnetic balls' centers. |
| through two three dimentional magnetic sensors and one three dimentional acceleration sensor inside the capsules, the position and orientation of the capsule can be calculated, and adjust the two balls so that the capsule is in the mid of two balls | adjust the two balls' XY plane location so that the capsule will move along the colon by the guidance of two magnetic balls. The same method can be used for the small bowl. |

SYSTEM AND METHOD FOR USING A CAPSULE DEVICE

TECHNICAL FIELD OF THE DISCLOSURE

This patent application relates to the art of capsule devices to be used in medical related applications, and more particularly, to systems to use two external magnetic generating means to navigate a magnetic capsule through a patient's GI track and methods of using the same.

BACKGROUND OF THE DISCLOSURE

The magnetic controllable capsule endoscope has been widely used commercially in the stomach examination and proved to be very successful. However, the same magnetically controlled capsule endoscope is not currently used to be placed inside the small bowl and colon to perform a routine examination.

To date, there are three types of external magnetic field generation systems to guide magnetic capsule endoscope devices while traveling in a patient's GI track. They are electromagnetic coils, electromagnet and permanent magnet. In order to meet the requirement of providing sufficient driving force, by external magnetic field or external magnetic gradient to move a typical magnetic capsule endoscope throughout a patient's small bowel, the power consumption for electromagnetic coils and electromagnet systems is very large, and the heat dissipation can make these systems even more bulkier and eventually very expensive to build and operate. Additionally, for electromagnetic coils and electromagnet systems, the electromagnetic compatibility (EMC) is also a big challenge, and potential safety issue relating to the electromagnetic field also post some concern.

Comparing to electromagnetic coils, the permanent magnet is a much more clean and efficient way to generate large magnetic field or field gradient. However, the control algorithm of the permanent magnet is much more complex than the electromagnetic coils. The electromagnet has a little bit more flexibility then the permanent magnet, since its strength can be adjusted by the current. However, for the control of the movement of the magnetic capsule, the electromagnet has the same order of the complexity of the permanent magnetic field. And to achieve the same magnetic field or field gradient, the electromagnet will occupy 2-3 times larger space than the permanent magnet. As for the permanent magnet, the sphere shape is the most efficient for the remote field or field gradient generation.

Therefore, magnetic control system to navigate a capsule through a small bowel is needed, the said system should employ an external permanent magnet dipole and easy to use.

SUMMARY OF THE INVENTION

The present invention discloses a system and method that can be used to examine a patient's GI track.

One technical problem solved by the present invention, is a magnetic capsule can be suspended in a target location without any physical support such as being supported by the wall, hanging from the top, or suspended in a liquid.

Another technical problem solved by the present invention, is that a magnetic capsule can move linearly both horizontally and linearly in a very controllable fashion, without any erratic movement.

Another technical problem solved by the present invention, is that a magnetic capsule can adjust orientation without being supported and degree of the adjustment is between 0-45 degrees.

Another technical problem solved by the present invention, is that a magnetic capsule can rotate smoothly, either vertical spin or planar rotation.

Another technical problem solved by the present invention, is that an overall movement of the capsule is contributed by two magnetic balls and two magnetic ball can work individually and coherently.

Another technical problem solved by the present invention, is that the overall movement of the capsule is contributed by two magnetic balls but at certain position or orientations of the magnetic capsule, one magnetic ball is a major movement contributor and the other magnetic ball is minor movement contributor, but at other positions or orientations, the two magnetic ball contributes equally to the movement of the magnetic capsule.

One advantage of the present invention, is that movement speed of the capsule can be adjusted in two independent ways, including movement of the magnetic balls in a certain movement direction and also under combined magnetic field strength.

On one hand, the present invention provides a variety of combinations of movement of the magnetic capsule, which are not possible before. On the other hand, the present invention provides a capsule to move within a confined area with defined route in a very controllable and tranquil manner.

Another advantage of the present invention is that the magnetic capsule can navigate make a smooth left turn and right turn along a colon channel. The magnetic capsule can turn from 0-360 degrees continuously.

In the scope of the present invention, the magnetic capsule can move linearly, including both horizontally and vertically, and the magnetic capsule can rotation and spin between 0-360 degrees continuously while maintaining its original position, and the orientation of the capsule can be adjusted accurately. By the combination of the horizontal and vertical rotation, the capsule can be orientated to any direction.

In one aspect of the present invention, a method for controlling movement of a magnetic capsule in a target area, is described. The method comprises introducing a magnetic capsule into a target area, said magnetic capsule has a longitude direction and the magnetic dipole placed inside the magnetic capsule has a magnetization direction coincide with the longitude direction of the magnetic capsule;

providing an external magnetic control system comprising more than one magnetic generation means;

moving the external magnetic control system to a first position with a first orientation, configured to move the magnetic capsule in a first movement direction, wherein the first movement direction coincide with the longitude direction of the magnetic capsule.

generating a combined external magnetic field configured to deliver a force to the capsule in the longitude direction of the magnetic capsule.

BRIEF DESCRIPTION OF THE DRAWINGS

Exemplary embodiments of the disclosure will be more clearly understood from the following detailed description taken in conjunction with the accompanying drawings in which:

FIG. 2 shows a perspective view of an exemplar external magnetic control system in accordance with aspects of the present invention; wherein the bed is extended outside of the supporting frames;

FIG. 3 shows a perspective view of an exemplar system in accordance with aspects of the present invention; wherein the bed is placed inside of the supporting frames;

FIGS. 21-24 are schematic illustration of how to rotate a magnetic capsule in xz plane;

FIGS. 27 and 28 show side views of a schematic diagram to illustrate how to adjust the position of the magnetic balls to move the magnetic capsule vertically; and FIG. 29 is a process flow diagram to show how the system is used.

DETAILED DESCRIPTION OF SELECTED EXAMPLES

Hereinafter, selected examples of a method of how to use a magnetic capsule device to be placed in a target location and system to use in order to accomplish the intended method steps to be described in detail with reference to the accompanying drawings. For simplicity purpose, the magnetic capsule is explained in the context of biomedical applications, i.e. the target location is an in vivo location, for example a location inside a digestive tract. For simplicity purpose, the medical device disclosed herein is designed to be placed in vivo. One of the non-invasive methods of delivery is by swallow into a digestive tract. Therefore, the medical device disclosed herein is referred as a capsule, which should not be construed as a limitation for its shape, dimension or size. The capsule device disclosed herein and methods of using the same can be implemented for many other applications beyond biomedical applications.

The system disclosed herein is for illustration purpose only, and should not be construed as limitations for what can and cannot be included in such a system. For the method disclosed herein to be accomplished, the system must include two primary magnetic generation means. In the method embodiments described below, the primary magnetic generation means are referred as magnetic balls. The two magnetic balls are illustrated as the same in size and magnetic strength. But this description of the two magnetic balls is only for simplification purposes. The method steps disclosed herein can be used any other two magnetic generation means, with a wide variety of relative size and weight and magnetic strength relationships. The two primary magnetic generations in the Figure illustrations are shown as arranged on opposites of a patient, specifically on top and bottom of the patient. These relative position arrangements between the patient and two magnetic balls should be construed as any limitations either. The two magnetic balls and patient can be arranged in accordance with its intended purposes, convenience and comfort to the patient, as long as the basic physical principles of the present invention is still withhold, then the method steps in the present invention are applicable to such a system.

Figure 1:
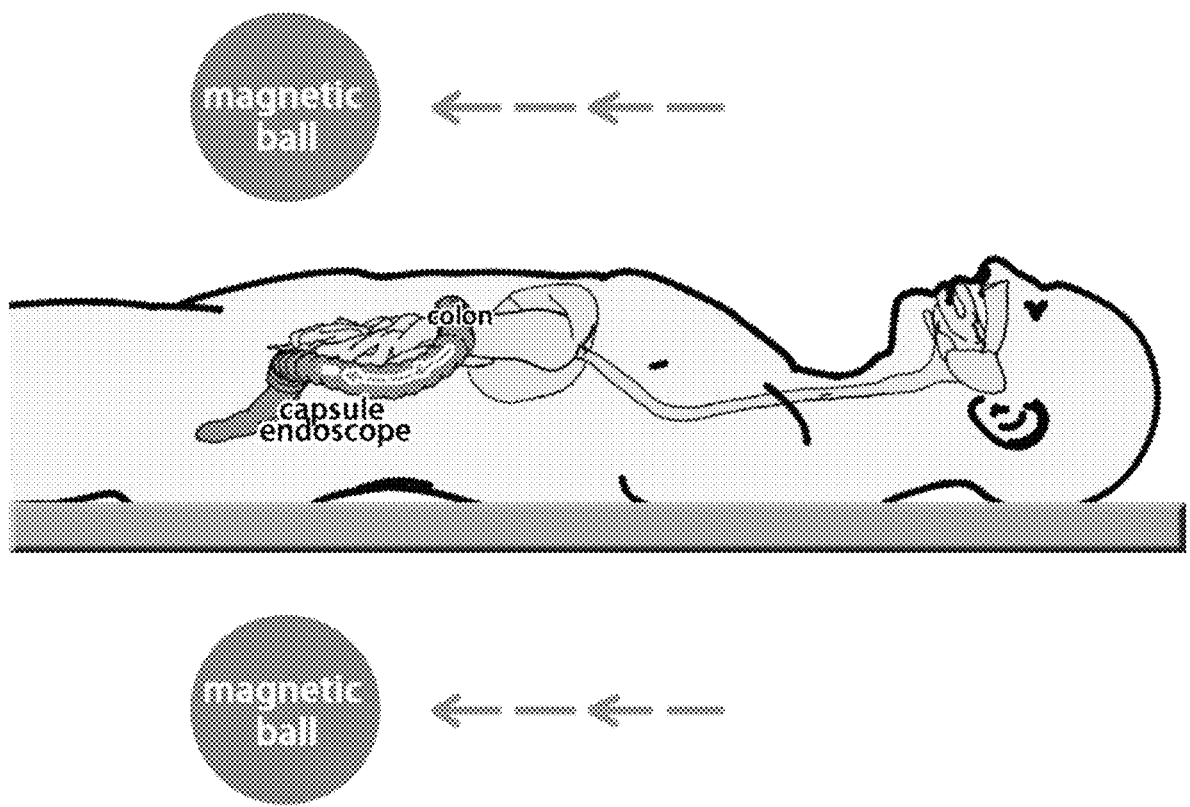
FIG. 1 shows a schematic illustration of a magnetic capsule system in accordance with aspect of the present invention.
Figure 4:
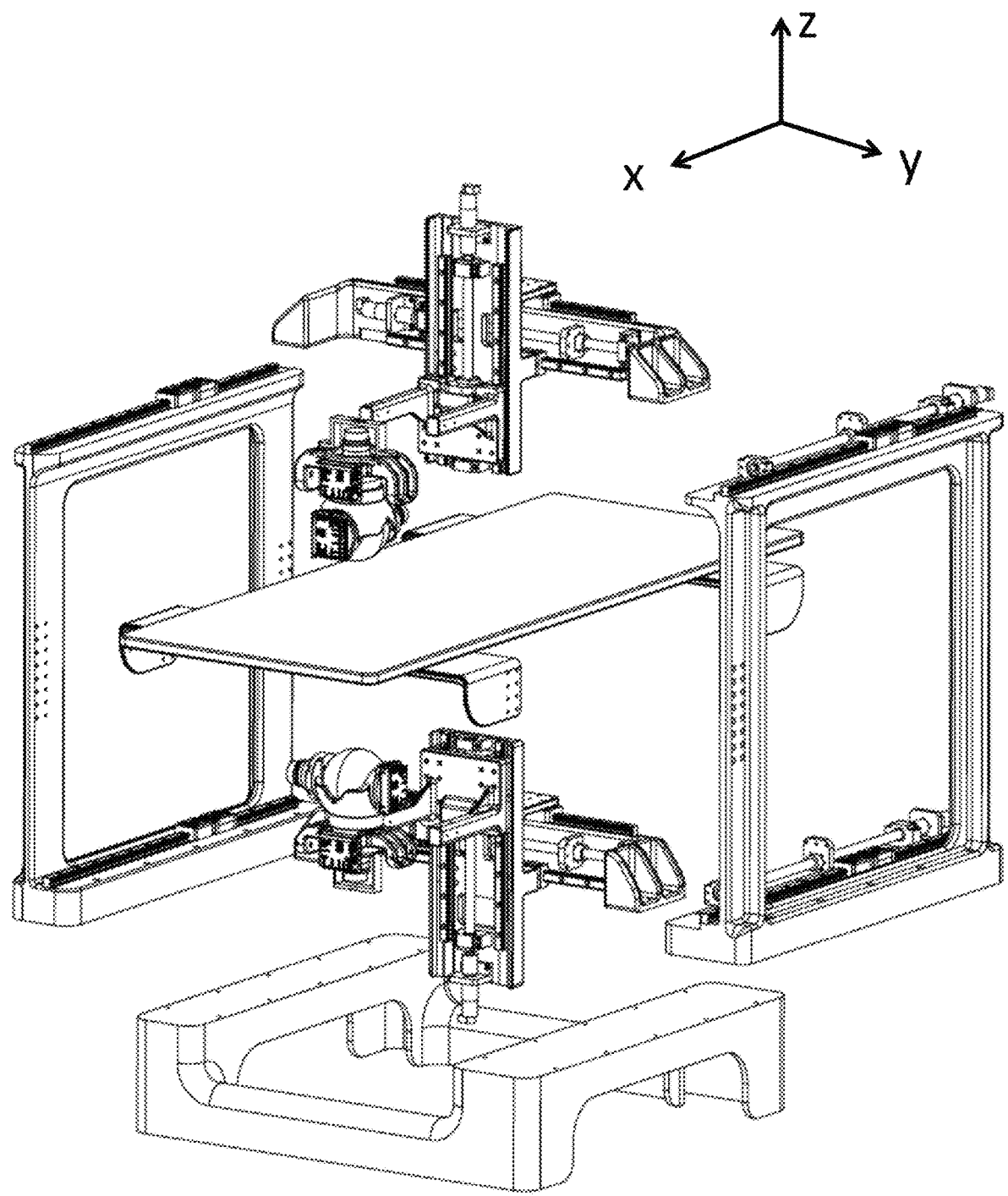
FIG. 4 shows an exploded perspective view of an exemplar system in accordance with aspects of the present invention; wherein the bed is placed inside of the supporting frames and assemblies are not placed together to better illustrate the system structure.
Figure 5:
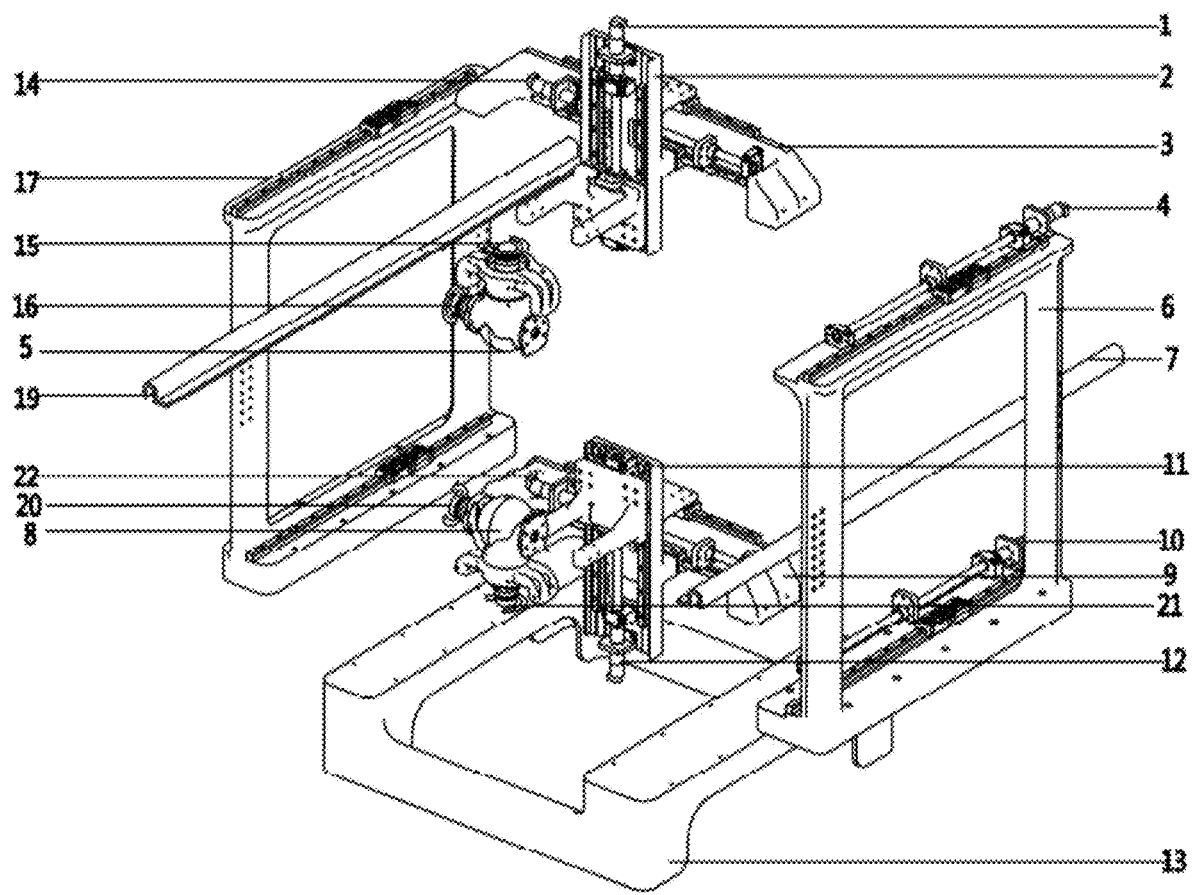
FIG. 5 shows an exploded perspective view of an exemplar system in accordance with aspects of the present invention, wherein the platform or bed is removed so that the structural components can be clearly displayed and labeled.
Figure 6:
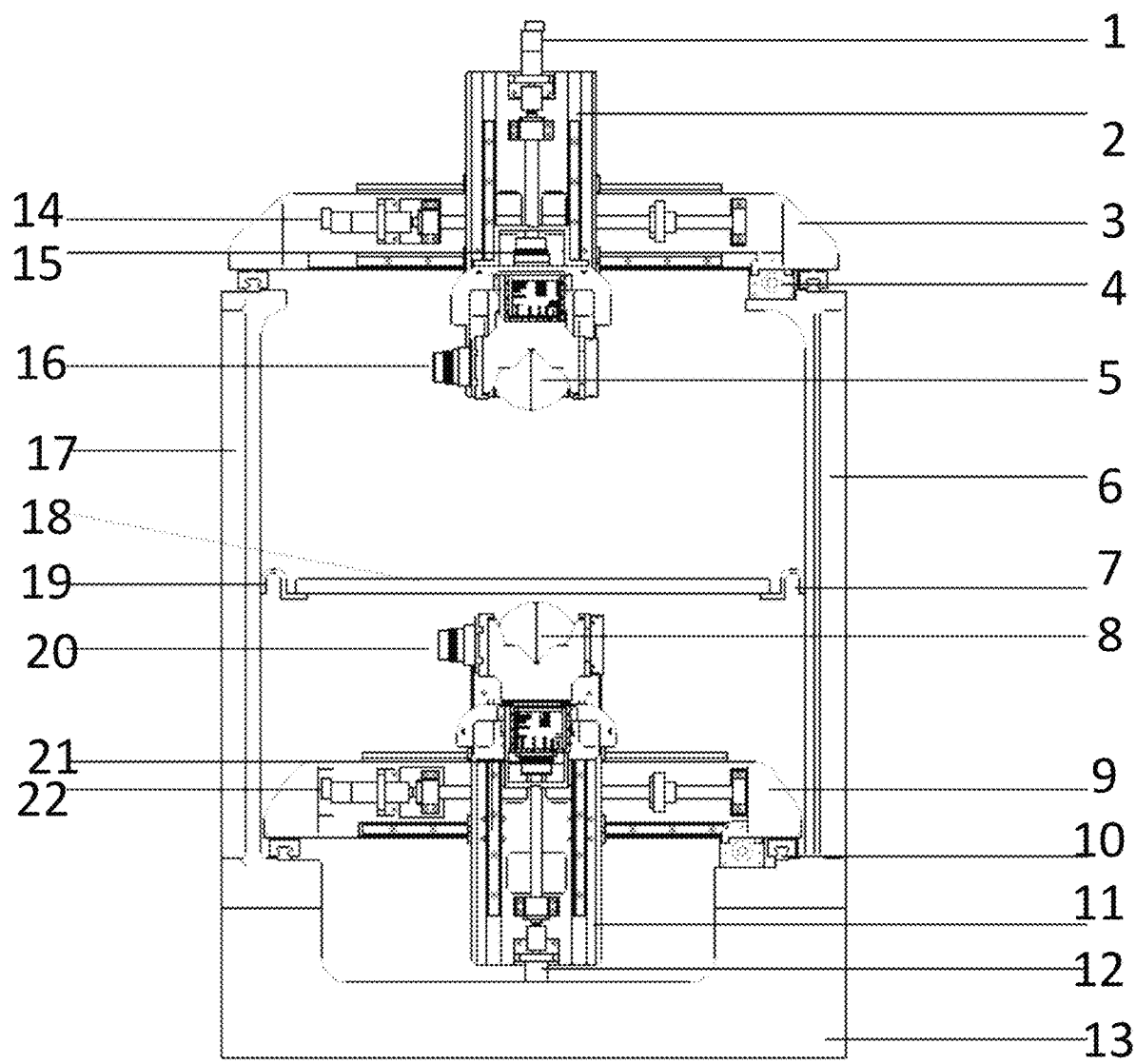
FIG. 6 is a cross sectional view of the external magnetic system, when viewing from the back of the external magnetic control system.
Figure 7:
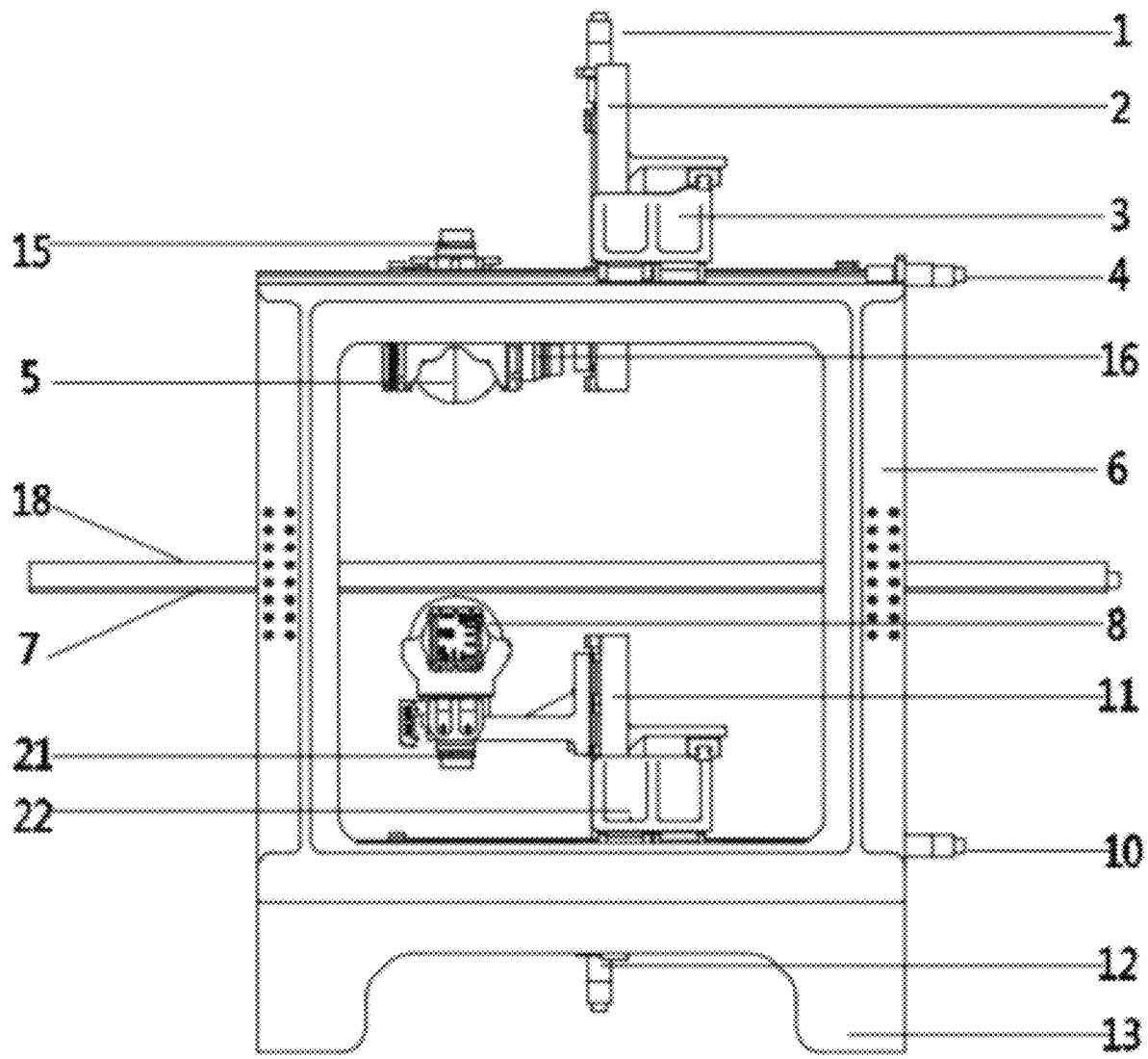
FIG. 7 is a left side view of the system of FIG. 6.
Figure 8:
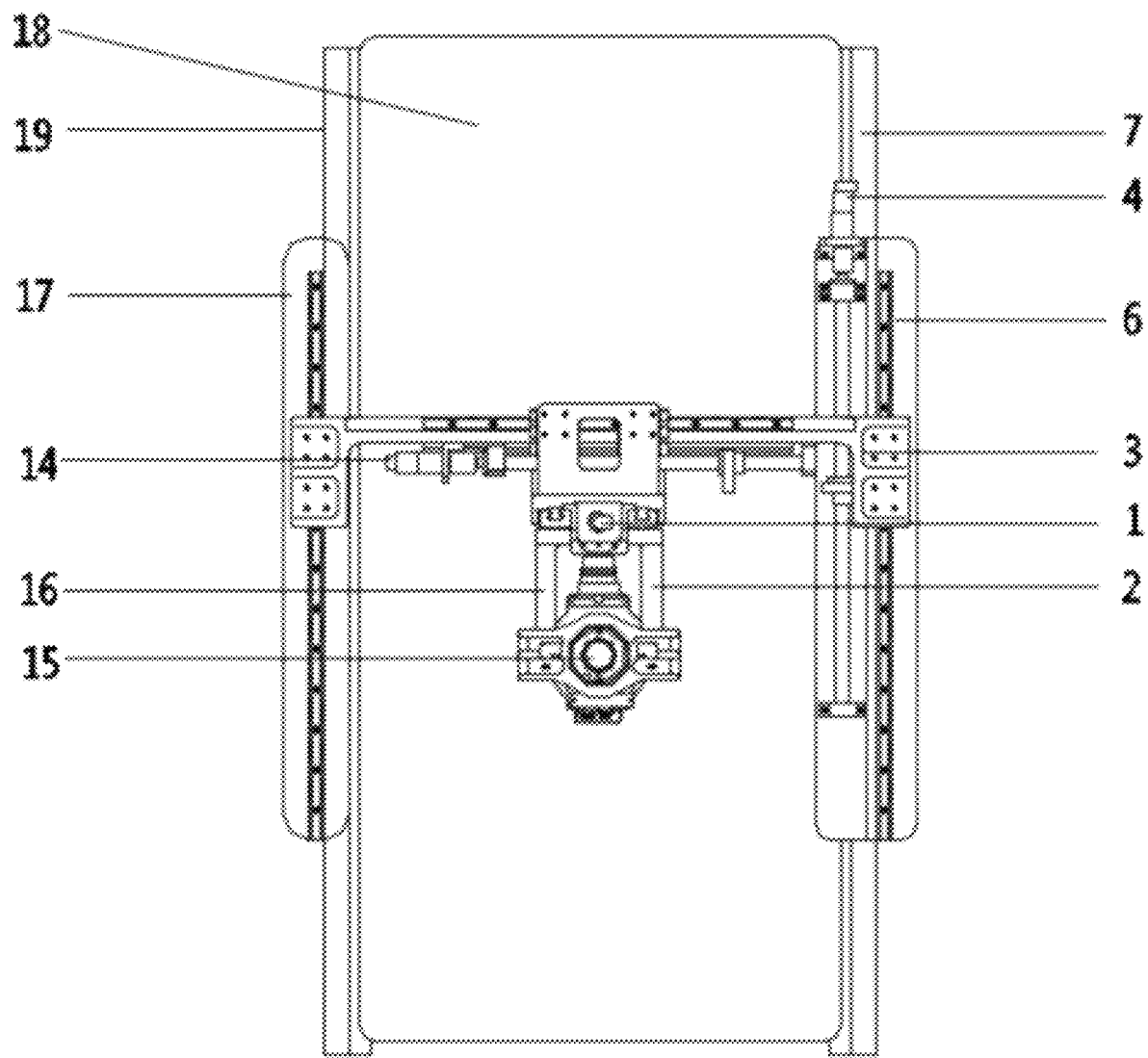
FIG. 8 is a top view of the system of FIG. 6.
Figure 9:
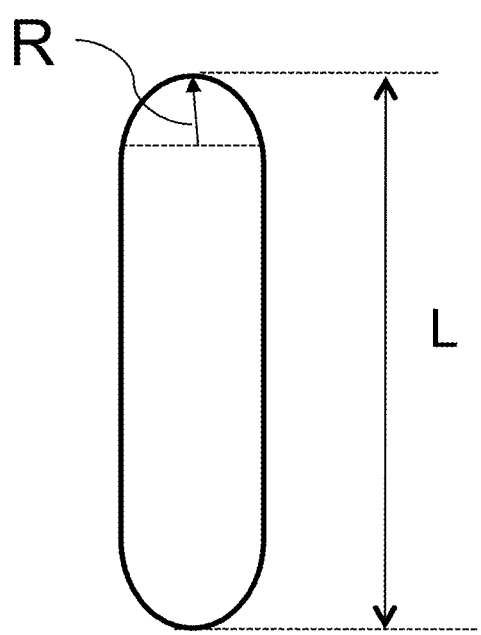
FIG. 9 is an illustration of a magnetic capsule in the accordance with the aspect of the present invention.

The magnetic capsule, according to FIG. 8, having a length, which is the longest dimension of the magnetic capsule. The length direction is referred as a longitude direction of the magnetic capsule. The magnetic capsule does not have to be the cylinder shape having one or two half domed ends as shown in FIG. 8. The capsule can be of any shape and weight as long as the fundamental physical principal is applicable to the magnetic capsule.

In a preferred example of the present invention, when the magnetic capsule moves linearly, the movement direction is the same as, coincide, or parallel as the longitude direction of the magnetic capsule. The magnetic capsule moves forward means the magnetic capsule moves having its front end pointing to the movement direction. The magnetic capsule moves backward means the magnetic capsule moves having its front end pointing to the opposite of the movement direction. The front end, in one preferred example, comprising a diagnostic means or therapeutic means, such as a camera. The back end, which is defined as linearly opposite to the front end, can also include a complimentary diagnostic means or therapeutic means in some examples. The magnetic capsule further has a magnetic dipole direction, which is parallel to the capsule longitude, either forward or backward.

In the scope of the present invention, M is a label for magnetic moment of the external magnetic generation means, which is the external magnetic ball; m is the magnetic moment of the magnet inside capsule. Generally, magnetic moment M for the magnetic balls is about 25-25000 $A/cm^2$, and magnetic moment m for the magnetic balls is about 0.02-2 $A/cm^2$.

In one example, the magnetic moment M for the magnetic balls is about 2000-3000 $A/cm^2$. In another example, the magnetic moment m for the magnetic balls is about 0.2 $cm^2$.

In the scope of the present invention, the external magnetic ball has a diameter of 8-10 cm, a minimum movement pathway is 30 cm in width, 30 cm in length and 20 cm in height; a maximum movement pathway is 60 cm in width, 100 cm in length and 50 cm in height; a preferred movement pathway is 40 cm in width, 60 cm in length and 30 cm in height.

In a first aspect of the present invention, the method disclosed herein is to the magnetic capsule can be introduced to a target location by using two external magnetic balls together, and the magnetic capsule is capable to be suspended with or without an additional support and/or form a physical contact with another a surface. Said surface includes, are not limited to an interior wall of a colon or a stomach, positioned on top of the magnetic capsule to allow the magnetic capsule to hang from; an interior wall of a colon or a stomach, positioned under the magnetic capsule to allow the magnetic capsule to stand on top of it; a liquid and an interface to allow the magnetic capsule to float therein. The magnetic capsule under the influence of the combined external magnetic filed generated by the two external magnetic balls, can be suspended in any media in the target examination area in any relative positions in order to accomplish its examination purpose.

The method steps include:
preparing a patient in an examination area, when capsule is inside the patient;
bringing two magnetic balls to the examination area;
positioning the two magnetic balls so that a distance the centers of the two magnetic balls are more than 50 cm in the vertical direction;
suspending the magnetic capsule in a media in a target area inside the patient, without forming any contact of an interior wall of the target area, wherein the media is air or $CO_2$;
measuring the resulted combined magnetic field by magnetic sensors inside the capsules;
calculating a position and orientation of the magnetic capsule by two three dimensional magnetic sensors and one three-dimensional acceleration sensor inside the capsules, the position and orientation of the capsule;
adjusting the vertical and horizontal position of the two magnetic balls so that the capsule is in a middle position of two magnetic balls.

In a second aspect of the present invention, the method disclosed herein is directed to allow a magnetic capsule, placed in a remote target area, to be moved linearly, including both horizontally.

Figure 10:
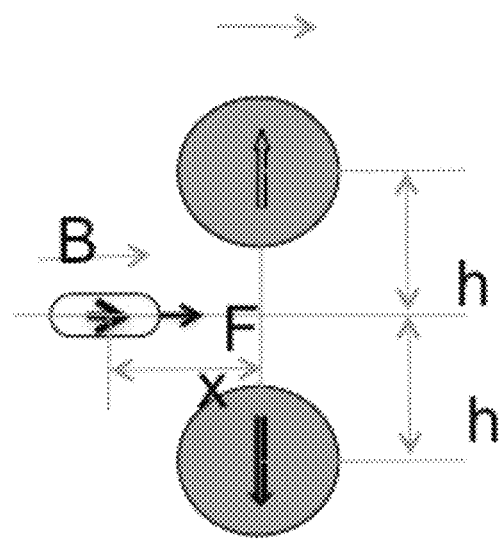
FIG. 10 is a schematic diagram to illustrate that capsule can move horizontally along an XY plane, wherein the capsule magnetization direction is the same as the forward movement direction.
Figure 11:
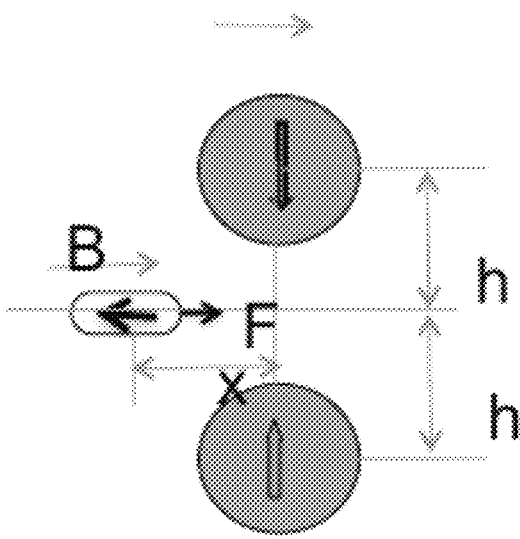
FIG. 11 is a schematic diagram to illustrate that a capsule can move vertically away from the XY plane in the z direction, wherein the capsule magnetization direction is the opposite to the forward movement direction.

Referring to FIGS. 10 and 11, the magnetic capsule provided herein are magnetic capsule endoscopes having imaging means such as a camera. The camera, in according to the convention of the art in the capsule endoscope, is positioned at the front end of the capsule if there is only one camera present in the capsule endoscope. In the schematic illustration of FIG. 10, the capsule endoscope has a camera on the right. The right end is the front end of the magnetic capsule endoscope and left end is the rear end of the magnetic capsule endoscope. The magnetic capsule endoscope has a magnetic dipole direction from left to right, i.e. from rear end of the capsule to the front end of the capsule, along its longitude direction. The indented movement direction is from the left to the right, moving forward. The combined external magnetic field generated is configured to move the capsule in its forward movement direction.

In this illustration in FIG. 10, the movement path is hypothetically designed to be along a central line across the capsule from the rear end to the front end, which is further extended forwardly to become a center dividing line between the two external magnetic balls. The two external magnetic balls are positioned on two opposing sides of the center dividing line. The center dividing line also set up as a movement boundary for the two external magnetic balls.

In FIG. 10, the two external magnetic balls are positioned in the examination area, one magnetic ball is positioned above the center dividing line, and the other is positioned below the center dividing line. Because in this example, the two magnetic balls having the same magnetic dipole and same size, therefore initially the two magnetic balls are positioned at equal distance away from the center dividing line. The distance is labeled as h in FIG. 10. Each of the magnetic balls has only one magnetic center. The magnetic centers of the two magnetic balls are aligned vertically and at the same time the magnetic dipole directions of the two magnetic balls are pointing to different directions. In FIG. 10, the magnetic ball above the center dividing line points up whereas the magnetic ball below the center dividing line points down. The two magnetic balls are positioned literally as a mirror image to each other across the center dividing line. The projection of the two magnetic centers of the two magnetic balls is ahead of the magnetic capsule in its movement direction. The distance between the projection and the center of the magnetic capsule is labeled as x. By positioning the upper and lower magnetic balls in this manner, the magnetic capsule moves forward toward the projection point under the combined magnetic field B, and applied the force F. Herein B is a vector and has a direction from left to right, which is the same as the movement direction. The force experienced by the magnetic capsule is a "drag forward."

Whereas, in FIG. 11, the magnetic capsule endoscope has a camera on the left. The left end is the front end of the magnetic capsule endoscope and the right end is the rear end of the magnetic capsule endoscope. The magnetic capsule endoscope has a magnetic dipole direction from right to left, i.e. from rear end of the capsule to the front end of the capsule, along its longitude direction. The indented movement direction is from the left to the right, moving backwards as to the magnetic capsule. The combined external magnetic field generated is configured to pull or drag the capsule in its backward movement direction.

In the illustration in FIG. 11, the movement path is also hypothetically designed to be along a central line across the capsule from the rear end to the front end, which is further extended forwardly to become a center dividing line between the two external magnetic balls. The two external magnetic balls are again positioned on two opposing sides of the center dividing line. The center dividing line also set up as a movement boundary for the two external magnetic balls.

Similarly, after the two external magnetic balls are positioned in the examination area, one magnetic ball is placed above the center dividing line, and the other is placed below the center dividing line. In this example, if the two magnetic balls are having the same magnetic dipole and same size, then initially the two magnetic balls are positioned at an equal distance away from the center dividing line. The distance is labeled as h in FIG. 11. If the two magnetic balls are having different size or at have different magnetic dipole, then difference between the two will be calculated and translated into differences in initial distance, as the goal of the present method is to provide an equal and harmonized magnetic field around the capsule in opposing directions so that the capsule can be moved in a tranquil stable manner. Each of the magnetic balls has only one magnetic center. The magnetic centers of the two magnetic balls are aligned vertically and at the same time the magnetic dipole directions of the two magnetic balls are pointing to different directions. In FIG. 11, the magnetic ball above the center dividing line points down, towards the center dividing line whereas the magnetic ball below the center dividing line points up, towards the center dividing line. The two magnetic balls are positioned literally as a mirror image to each other across the center dividing line. The projection of the two magnetic centers of the two magnetic balls is ahead of the magnetic capsule in its movement direction. The distance between the projection and the center of the magnetic capsule is labeled as x. By positioning the upper and lower magnetic balls in this manner, the magnetic capsule moves forward toward the projection point under the combined magnetic field B, and applied the force F. Herein B is a vector and has a direction from left to right, which is the same as the movement direction. The force experienced by the magnetic capsule is a "drag backward."

In a second aspect of the present invention, the method is directed to move the magnetic capsule endoscope horizontally forwardly or backwardly along the longitude direction of the magnetic capsule endoscope, by moving the two external magnetic balls horizontally, wherein the magnetization direction of magnetic capsule endoscope, the combined magnetic field (B) direction and direction of the force (F) received by the magnetic capsule endoscope are all parallel to one another. The intended movement direction of the magnetic capsule points toward the connecting line between the two centers of the two external magnetic balls. In a preferred embodiment, a maximum point of the combined magnetic field (B) and a maximum point of the force (F) received by the magnetic capsule are in very close proximity to teach other.

FIGS. 10 and 11 show two examples of linear movement embodiment according to the aspects of the present invention. In this method, the two magnetic balls are vertically aligned on opposing areas where the center dividing line serves as a boundary. The center dividing line is also a proposed movement direction of the magnetic capsule. The magnetization directions of the two external magnetic balls are perpendicular to the center dividing line and opposite to each other, either both pointing to the center dividing line at the same time or pointing away from the center dividing line at the same time. The magnetic capsule endoscope is positioned having its longitude direction along the center dividing line. And it is required that the magnetization direction of the magnetic capsule lays horizontally along its long its length. The force F and magnetic field B received by the magnetic capsule are normalized by their maximum value. The distance from each center of the magnetic ball to the center dividing line is labeled as h. Distance from the magnetic center of the magnetic capsule to the projection line, connecting to the two magnetic centers of the external magnetic ball, is distance x. And distance x can be normalized by distance h.

$$F = \frac{\mu_0}{4\pi} \frac{18\,Mmhx^2}{(x^2+h^2)^{7/2}} \qquad \text{Equation 1}$$

$$B = \frac{\mu_0}{4\pi} \frac{6\,Mhx}{(x^2+h^2)^{5/2}} \qquad \text{Equation 2}$$

$$F_{max} = \frac{\mu_0}{4\pi} \frac{2.2\,Mm}{h^4}, \text{ when} \qquad \text{Equation 3}$$
$$x = 0.63\,h,\ B = \frac{\mu_0}{4\pi} \frac{1.64\,M}{h^3}$$

$$B_{max} = \frac{\mu_0}{4\pi} \frac{1.7\,M}{h^3}, \text{ when} \qquad \text{Equation 4}$$
$$x = 0.5\,h$$

The relationship between distance x, distance h, and force F and combined magnetic field B can be represented by the Equations 1 and 2, wherein M is magnetic moment of magnetic ball, m is the magnetic moment of the magnet inside capsule, $u_0$ is vacuum magnetic permeability.

The maximum value of $F_{max}$ and $B_{max}$ can also be calculated according to Equation 3 and Equation 4.

Figure 12:
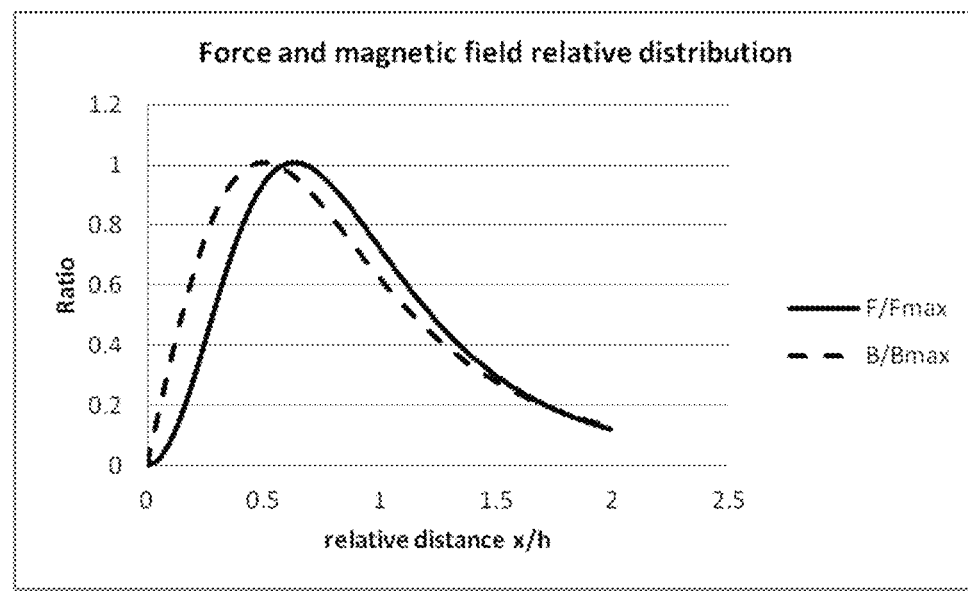
FIG. 12 is a force and magnetic field relative distribution chart when the positions of the two magnets and magnetic capsule are as listed in FIG. 11.

FIG. 12 shows a relationship between ratio $B/B_{max}$ and relative distance x/h, and a relationship between ratio $F/F_{max}$ and relative distance x/h. As the calculation and FIG. 12 show, an ideal movement region to achieve most stable movement occurs when distance x is between 0.5 h to 0.7 h, at that time both magnetic force (F) and magnetic field strength (B) are strong. In this example, h is about 15 cm and corresponding distance x is about 7.5-10.5 cm. In this example, M is magnetic moment of magnetic ball, m is the magnetic moment of the magnet inside capsule, $u_0$ is vacuum magnetic permeability.

In accordance with the aspect of the present invention, in one example, the distance h is about 5-25 cm and distance x is about 2.5-17.5 cm. In another example, distance h is about 10-20 cm and distance x is about 5-14 cm. In another example, distance h is about 12-17 cm and distance x is about 6-11.9 cm.

Figure 13:
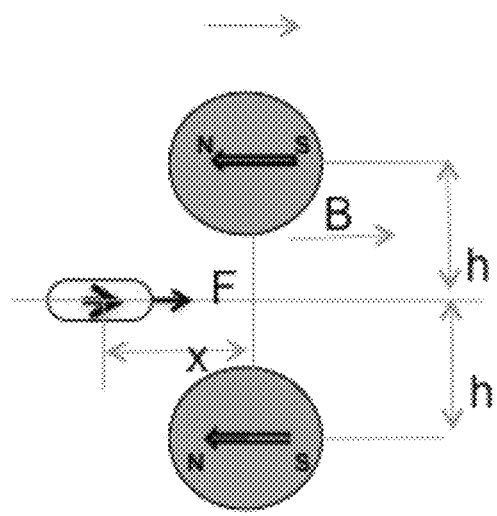
FIG. 13 is a schematic illustration of another operation condition wherein the magnetizations of the two magnets are opposite to the magnet capsule.
Figure 14:
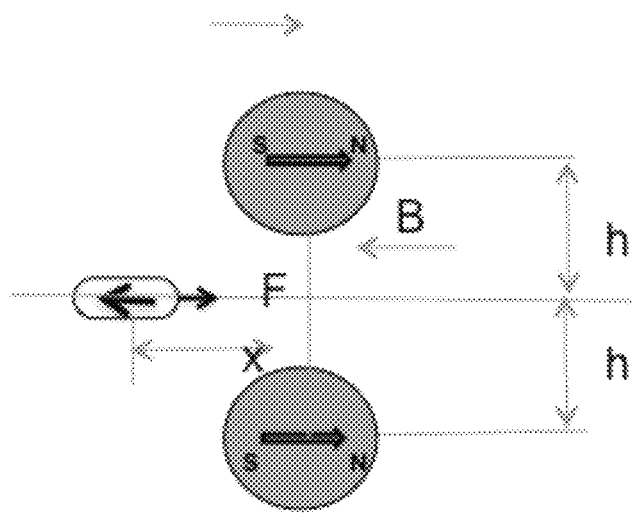
FIG. 14 is a force and magnetic field relative distribution chart when the positions of the two magnets and magnetic capsule are as listed in FIG. 13.
Figure 15:
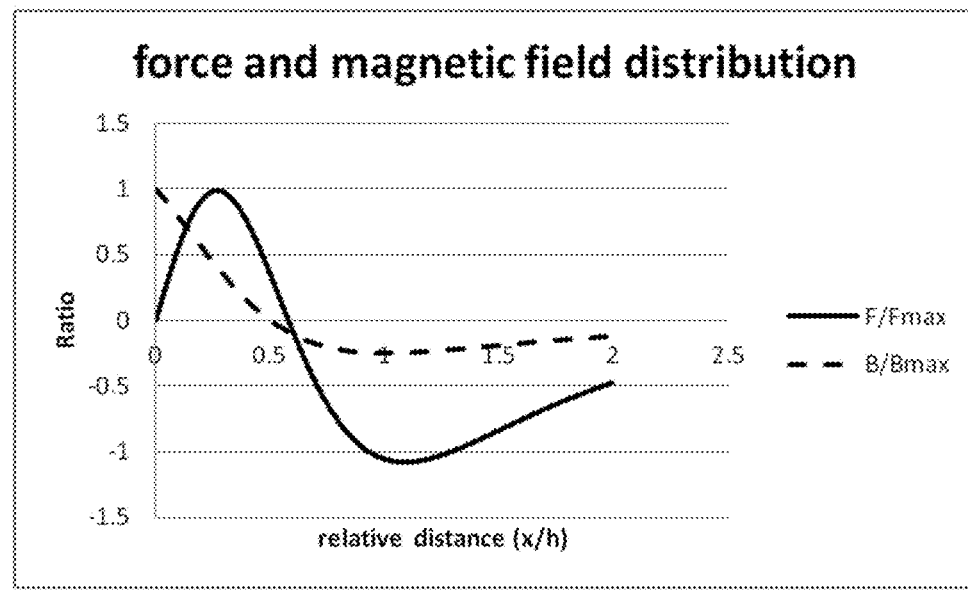
FIG. 15 is schematic illustration of another operation condition wherein two magnetic balls are aligned vertically; their magnetizations of both balls are same and the magnetization directions are mirror image to each other along the middle plane between them.

FIGS. 13-15 describe a third aspect of the present invention. Referring to FIGS. 13 and 14, the magnetic capsule is placed in a way that the movement direction is its length direction. In FIG. 13, the front end of the magnetic capsule in on the right, the magnetization direction of the capsule goes from left to right. The middle line along the longitude direction of the capsule extends to become a center dividing line of the external magnetic control system. The center dividing line coincides with the proposed movement direction of the magnetic capsule. The two external magnetic balls are positioned on two different sides of the center dividing line and their respective projection positions on the center dividing line are ahead of the magnetic capsule. Referring to FIG. 13, the two magnetic balls are positioned above and below the center dividing line, having their magnetic centers are mirror image to each other. A projection line, connecting the centers of the two magnetic balls, perpendicular to the center dividing line, which is also an extension line of the longitude of the magnetic capsule. The distance between the magnetic center of the capsule to the projection line, or the cross point between the projection line and center dividing line is x. The distance between the center (magnetic center) of the external magnetic ball to the center dividing line is h. In FIG. 13, both external magnetic balls are made of same material, having the same dimensions; therefore, initially both magnetic balls are positioned at the equal distance to the center dividing line. One key difference between the embodiment in FIG. 13 and the embodiment in FIG. 10 is that the magnetic directions of the upper magnetic ball and lower magnetic ball are parallel to the magnetic direction of the magnetic capsule, instead of perpendicular, but having opposite directions. In FIG. 13, the magnetic direction of the magnetic capsule is from left to right, whereas the magnetic directions of the upper and lower magnetic balls are from right to left. In the example shown in FIG. 13, the centers of the upper and lower magnetic balls and the magnetic center of the magnetic capsule are in the same vertical plane. The combined magnetic field B points to the movement direction, which is to the right and the force received by the magnetic capsule also points to the forward direction, to the right and the magnetic capsule is dragged forward.

FIG. 14 schematically illustrates an alternative embodiment of what is described in FIG. 13, wherein the magnetic capsule is dragged backwards instead of forward. In FIG. 14, the front end of the magnetic capsule in on the left, the magnetization direction of the capsule goes from right to left. The middle line along the longitude direction of the capsule extends to become a center dividing line of the external magnetic control system. The center dividing line coincides with the proposed movement direction of the magnetic capsule. Similarly, the two external magnetic balls are positioned on two different sides of the center dividing line and their respective projection positions on the center dividing line are ahead of the magnetic capsule in the proposed movement pathway. Referring to FIG. 14, the two magnetic balls are positioned above and below the center dividing line, having their magnetic centers are mirror image to each other. A projection line, connecting the centers of the two magnetic balls, perpendicular to the center dividing line, which is also an extension line of the longitude of the magnetic capsule. The distance between the magnetic center of the capsule to the projection line, or the cross point between the projection line and center dividing line is x. The distance between the center (magnetic center) of the external magnetic ball to the center dividing line is h. In FIG. 14, both external magnetic balls are made of same material, having the same dimensions; therefore, initially both magnetic balls are positioned at the equal distance to the center dividing line. One key difference between the embodiment in FIG. 14 and the embodiment in FIG. 11 is that the magnetic directions of the upper magnetic ball and lower magnetic ball are parallel to the magnetic direction of the magnetic capsule, instead of perpendicular, but having opposite directions. In FIG. 14, the magnetic direction of the magnetic capsule is from right to left, whereas the magnetic directions of the upper and lower magnetic balls are from left to right. In the example shown in FIG. 14, the centers of the upper and lower magnetic balls and the magnetic center of the magnetic capsule are in the same vertical plane. The combined magnetic field B direction is from right to left, and the force received by the magnetic capsule moves the magnetic capsule from left to the right, and the magnetic capsule is dragged backwardly.

A key difference between embodiments described in FIGS. 13 and 14 and embodiments described in FIGS. 10 and 11, are the magnetic directions of the two external magnetic balls. In the embodiments illustrated in FIGS. 10 and 11, the magnetic balls having a magnetic direction perpendicular to the magnetic direction of the magnetic capsule, whereas in the embodiments illustrated in FIGS. 13 and 14, the magnetic balls having a magnetic direction parallel to the magnetic direction of the magnetic capsule. Both embodiments can provide a horizontal stable movement to the magnetic capsule, however the max force (F) experienced by the magnetic capsule in FIGS. 13 and 14 are about half of the max force (F) experienced by same magnetic capsule in FIGS. 10 and 11.

In the third aspect of the present invention, the method is directed to move the magnetic capsule endoscope horizontally, forwardly or backwardly along the longitude direction of the magnetic capsule endoscope, by moving the two external magnetic balls horizontally, wherein the magnetization direction of magnetic capsule endoscope, the combined magnetic field (B) direction and direction of the force (F) received by the magnetic capsule endoscope are all parallel to one another, but the intended movement direction is parallel to magnetization directions of the two external magnetic balls. In general, magnetic field generated by the external magnetic ball is distributed in three dimensions, the magnetic fields from the two external magnetic balls are combined to form a combined external control magnetic field. Theoretically, there is no space limitation of the magnetic field, but it will be decayed in the inverse power of 3. Therefore, in a preferred embodiment, the two external magnetic balls present in the same vertical plane with the magnetic capsule to ensure most optimal performance.

$$F = \frac{\mu_0}{4\pi} \frac{6\ Mm(h/x)(1-3(x/h)^2)}{h^4(1+(x/h)^2)^{7/2}} \quad \text{Equation 5}$$

$$B = \frac{\mu_0}{4\pi} \frac{2\ M(1-2x/h)}{(1+(x/h)^2)^2} \quad \text{Equation 6}$$

$$F_{max} = \frac{\mu_0}{4\pi} \frac{Mm}{h^4}, \text{ when} \quad \text{Equation 7}$$
$$x = 0.26\ h,\ B = \frac{\mu_0}{4\pi} \frac{0.42\ M}{h^3}$$

$$B_{max} = \frac{\mu_0}{4\pi} \frac{2\ M}{h^4}, \text{ when} \quad \text{Equation 8}$$
$$x = 0$$

The relationship between distance x, distance h, and force F and combined magnetic field B can be represented by the Equations 5 and 6, wherein M is magnetic moment of magnetic ball, m is the magnetic moment of the magnet inside capsule, u0 is vacuum magnetic permeability.

The maximum value of $F_{max}$ and $B_{max}$ can also be calculated according to Equations 7 and Equation 8.

FIG. 15 shows a relationship between ratio $B/B_{max}$ and relative distance x/h, and a relationship between ratio $F/F_{max}$ and relative distance x/h.

In order to make the force and magnetic field in the same direction, the capsule magnet and two magnetic balls shall be in the same vertical plane. If it is not in the same vertical plane, there will be a force on capsule pointing to the vertical plane besides the same direction force.

As the calculation results according to equations 5-8 and FIG. 15 first shows, an optimal movement region to achieve strongest magnetic force (F) occurs when distance x is about 0.26 h. In this example, h is generally about 15 cm and corresponding distance x is about 4 cm. In the embodiments illustrated in FIGS. 13 and 14, the magnetic capsule movement direction is x direction, up and down direction is the z direction, the in and out of the plane direction is a y direction. When the value of distance x is 4 cm, suggest that the magnetic ball movement area in XY plane needs to be 4 cm larger than the active colon examination area in all directions on the xy plane, including each +x, −x, +y, −y direction.

Secondly, FIG. 15 also suggests when the distance x is larger than 0.5 h, the combined magnetic field will change its direction, thus the capsule will also have to change its direction to be stable in the region larger than 0.5 h.

Figure 16:
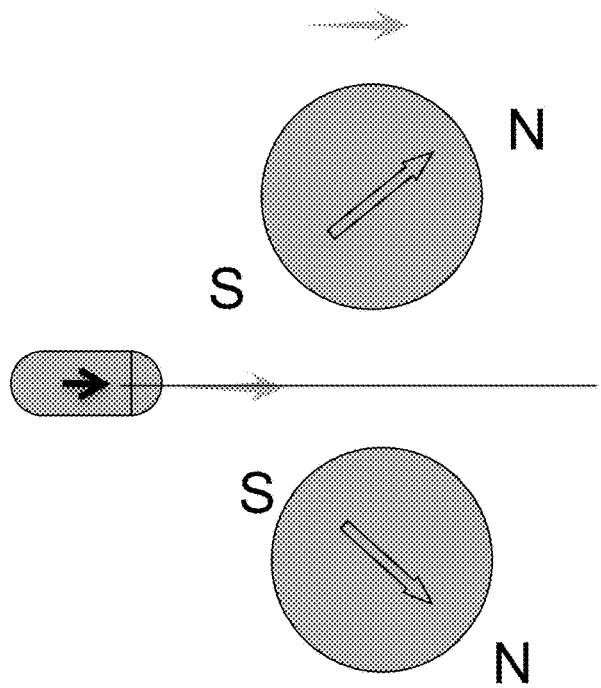
FIG. 16 is schematic illustration of another operation condition wherein two magnetic balls are aligned vertically, their magnetizations of both balls are same and the magnetization directions are mirror image to each other along the middle plane between them, and wherein the magnetic capsule is dragged forward.
Figure 17:
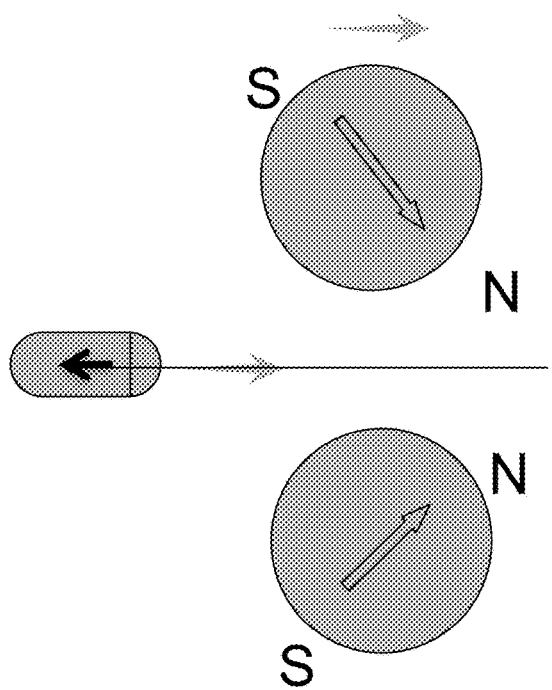
FIG. 17 is schematic illustration of another operation condition wherein two magnetic balls are aligned vertically, their magnetizations of both balls are same and the magnetization directions are mirror image to each other along the middle plane between them, and wherein the magnetic capsule is dragged forward.

FIGS. 16-17 describe a fourth aspect of the present invention, wherein the magnetic directions of the two external magnetic balls are neither perpendicular nor parallel to the magnetic direction of the magnetic capsule but forming a angel between 0-90 degrees. Referring to FIGS. 16 and 17, for comparison purposes, with embodiments in FIGS. 10-11 and 13-14, the magnetic capsule is placed in a way that is the same as those embodiments, that is the magnetic capsule is placed in horizontally in the xy plane, and the movement direction is in its length direction-x direction. In FIG. 16, the front end of the magnetic capsule is on the right, the magnetization direction of the capsule goes from left to right. The middle line along the longitude direction of the capsule extends to become a center dividing line of the external magnetic control system. The center dividing line coincides with the proposed movement direction of the magnetic capsule. The two external magnetic balls are positioned on two different sides of the center dividing line and their respective projection positions on the center dividing line are ahead of the magnetic capsule. Referring to FIG. 16, the two magnetic balls are positioned above and blow the center dividing line, having their magnetic centers are mirror image to each other. A projection line, connecting the centers of the two magnetic balls, perpendicular to the center dividing line, which is also an extension line of the longitude of the magnetic capsule. The distance between the magnetic center of the capsule to the projection line, or the cross point between the projection line and center dividing line is x. The distance between the center (magnetic center) of the external magnetic ball to the center dividing line is h. In FIG. 13, both external magnetic balls are made of same material, having the same dimensions; therefore, initially both magnetic balls are positioned at the equal distance to the center dividing line.

The magnetization of the external magnetic balls can be derived into parallel and perpendicular components, then the examples and operation principles described in FIGS. 10-15 can be used in a combinatory manner, including parallel and perpendicular component all are in the same vertical plane.

Figures 18A, 19:
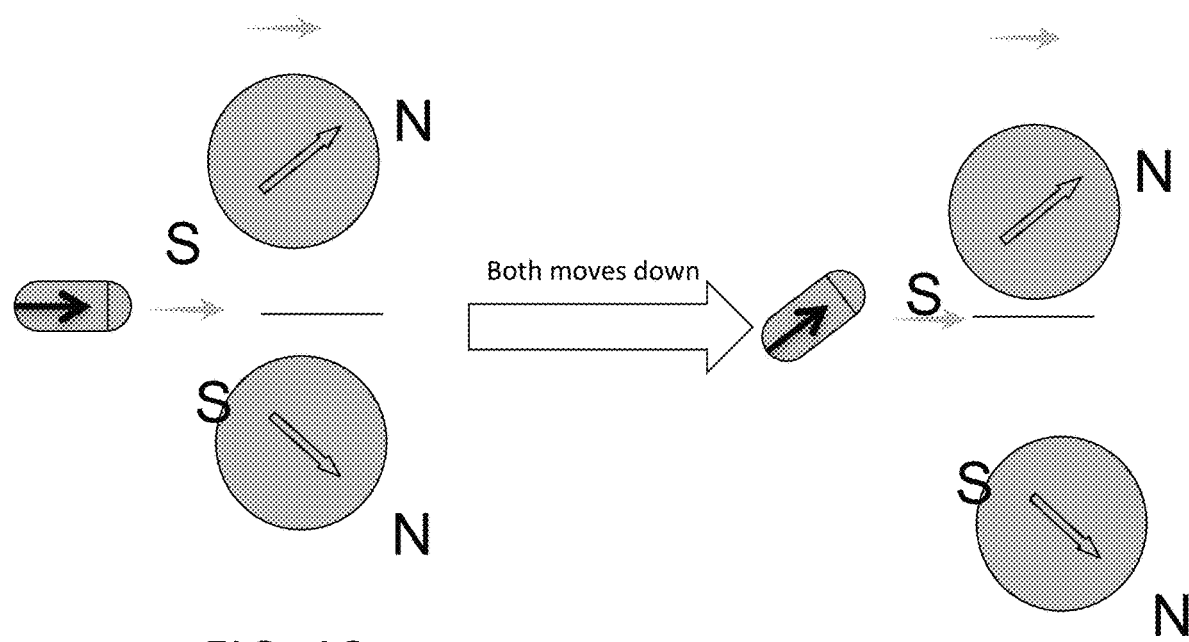
FIG. 18a and FIG. 18b illustrate initial position and orientation of the magnetic capsule and external magnetic balls in a process to change a magnetic capsule through the adjustment in the external magnetic system.
FIG. 19 is a finished position and orientation of the magnetic capsule and external magnetic balls in a process to change a magnetic capsule through the adjustment in the external magnetic system.

In accordance with the aspects of the present invention, the magnetic capsule endoscope disclosed herein can not only moves horizontally in a stable manner but change orientation as well. One way is to move the external magnetic balls in a synchronized manner along the vertical direction (FIG. 19). Another way is to spin both magnetic balls vertically (FIG. 20).

Figures 18B, 20:
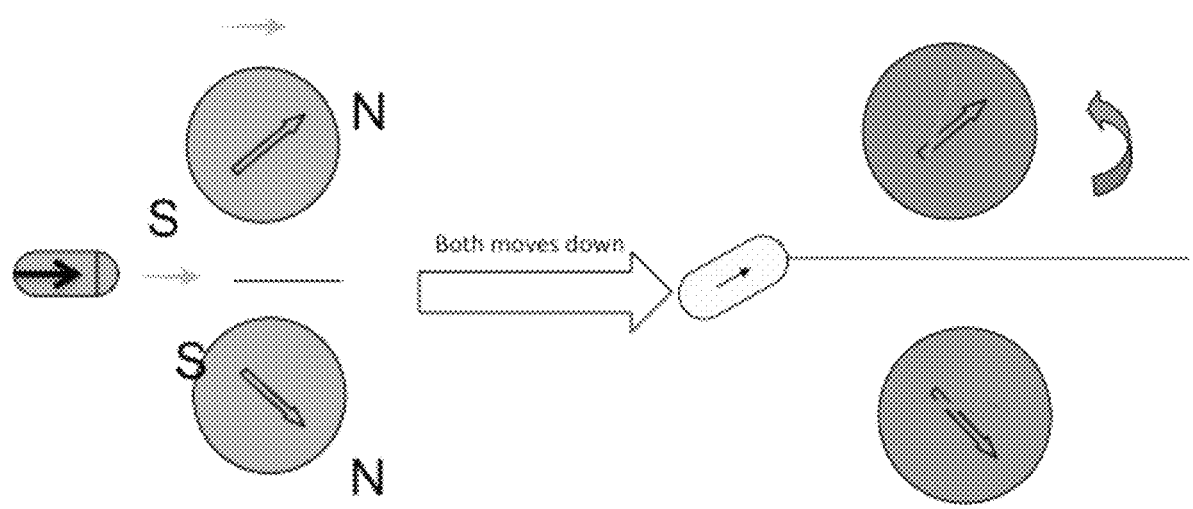
FIG. 20 is another finished position and orientation of the magnetic capsule and external magnetic balls in an alternative process to change a magnetic capsule through the adjustment in the external magnetic system.

Referring to FIGS. 18a-b and FIG. 19, it describes that the magnetic capsule endoscope can look up and down without changing its relative position in the target area, that is maintaining its position in x and y direction. In FIGS. 18a-b, the magnetic capsule start from a position laid horizontally on a xy plane, its length direction elongated along a x direction, whereas the two magnetic balls having a magnetic direction forming an angle between 0-90 degrees with the magnetic direction of capsule endoscope. The front end of the magnetic capsule is on the right. The proposed movement direction can be to the right after the orientation adjustment. As FIG. 19 shows, when both external magnetic balls move vertically down along the a direction without moving horizontally in x or y direction, the magnetic capsule will look up while maintaining its magnetic center at its original position in the xy plane. In the same fashion, from the original position on the left as shown in FIGS. 18a-b, if both the external magnetic moves synchronized matter upwardly, then the magnetic capsule will look down.

In a fifth aspect of the present invention, orientation of the magnetic capsule endoscope can be adjusted by moving both the two external magnetic balls along the z direction.

In one embodiment, the magnetic capsule endoscope can look up from a laid down position when both external magnetic balls along the z direction are moved downwardly along z direction.

In an alternative embodiment, the magnetic capsule endoscope can look down from a laid down position when both external magnetic balls along the z direction are moved upwardly along the z direction.

FIGS. 18a-b and FIG. 20 describe an embodiment method that the orientation of the magnetic capsule can be changed without changing the positions of the two external magnetic balls, specifically, the positions of the magnetic centers remains unchanged when the front end or back end orientation of the magnetic capsule are changed. Wherein the orientation change means only just a pasture of the capsule is changed, the position of its magnetic center is not changed.

In a sixth aspect of the present invention, orientation of the magnetic capsule endoscope can be adjusted by spinning the external magnetic balls simultaneously around z axis or vertical axis.

Besides moving horizontally in a stable manner, changing orientation without changing position, in accordance with the aspects of the present invention, the magnetic capsule endoscope disclosed can also rotate either changing its position or not changing its relative position.

If the capsule is close to one magnetic sphere and far away from another magnetic sphere, the capsule will be largely controlled by one magnetic ball, either the upper one or the lower one. In this case, the capsule control behavior is the same as the signal magnetic ball. It will be reduced to the patents we applied before.

In a seventh aspect of the present invention, the magnetic capsule can be rotated in 0-90 degrees without changing its position. Before the rotation, the magnetic capsule having its magnetic direction perpendicular to the center dividing line and two magnetic balls having their magnetic directions forming an angle of 0-90 degrees with the center dividing line and during the rotation process, only the upper magnetic ball rotate counter clockwise and the lower magnetic ball is kept still to maintain its position and orientation. In this example, one magnetic ball is the primary magnetic ball and the other magnetic ball is a secondary magnetic ball. The rotational magnetic filed is contributed primary from the primary magnetic ball. In one example, the magnetic capsule is placed closer to the primary magnetic ball than to the secondary magnetic ball. In another example, the rotation of the magnetic capsule is limited to rotate in 0-90 degrees while the back end of the magnetic capsule is anchored on either a upper interior wall or lower interior wall of the colon.

FIGS. 21-24 describe another method to rotate the magnetic capsule vertically in a xz plane. The rotation of the magnetic capsule can happen between 0-360 degrees in either a clock wise or counter clockwise manner. In this embodiment, FIG. 22 depicts a start position of the rotation. FIGS. 22-23 shows intermediate rotation positions. As in the start position shown in FIG. 21, the two external magnetic balls are arranged on opposing sides of a patient. A center dividing line is formed in between the two magnetic balls having a both balls are arranged at an equal distance to the center dividing line. The magnetic direction of the magnetic capsule is perpendicular to the center dividing line. Both magnetic balls also have magnetic direction parallel to the magnetic capsule and perpendicular to the center dividing line, also the both magnetic directions are the same to the magnetic capsule. Upon turning the magnetic balls clockwise, the capsule rotate counter clock wise to the left (FIG. 22), then downwardly (FIG. 23) and to the right (FIG. 24). In all the movement sequences, both magnetic balls move simultaneously to achieve the balanced the magnetic field for 0-360 degree rotation.

In an eight aspect of the present invention, another method to rotate or vertically rotate the magnetic capsule without changing the positions of the magnetic capsule is disclosed, herein vertical rotation means rotation along the xz plane. In this embodiment, the two magnetic ball moves simultaneously and magnetic capsule rotates counter clockwise in 0-360 degrees in response to a clock wise vertical rotation 0-360 degrees. In a first start position, the magnetic direction of the magnetic capsule is perpendicular to the center dividing line whereas both magnetic balls are having magnetic direction parallel to the magnetic direction of the capsule and all point to the top. In a second start position, the magnetic direction of the magnetic capsule is parallel to the center dividing line whereas both magnetic balls are having magnetic direction parallel to the magnetic direction of the capsule, both magnetic balls point to the right whereas the magnetic capsule point to the left. In a third start position, the magnetic direction of the magnetic capsule is perpendicular to the center dividing line whereas both magnetic balls are having magnetic direction parallel to the magnetic direction of the capsule and all point downwardly. In a fourth start position, the magnetic direction of the magnetic capsule is parallel to the center dividing line whereas both magnetic balls are having magnetic direction parallel to the magnetic direction of the capsule, the magnetic capsule points to the right and two magnetic ball point to the left.

Figure 25:
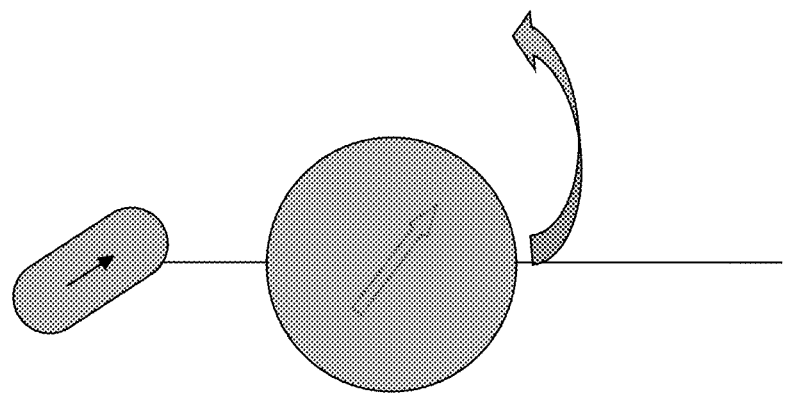
FIG. 25 is a top view of a schematic illustration of how to rotate a magnetic capsule in xy plane.
Figure 26:
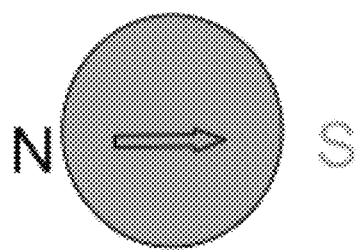
FIG. 26 shows a side view of a schematic diagram to how to spin a magnetic capsule in xy plane.
Figure 26:
Figure 26:
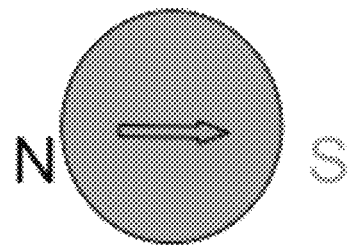

FIGS. 25-26 describe a method to rotate the magnetic capsule horizontally in a xy plane around its own magnetic center. FIG. 25 is a top view and FIG. 26 is a side view. In order to achieve a horizontal rotation along a xy plane, the magnetic capsule is laid horizontally on the xy plane. The magnetic direction of the two external magnetic balls are parallel to the magnetic direction of the magnetic capsule. The magnetic directions of the two magnetic balls point to right and magnetic capsule has a magnetic direction point to the left. Then upon a simultaneous horizontal rotation of the two external magnetic balls in a counter clockwise manner, the magnetic capsule in the xy plane will respond with a horizontal rotation in a synchronized manner, having the same rotation direction.

In a ninth aspect of the present invention, another method to rotate or horizontally rotate the magnetic capsule without changing the positions of the magnetic capsule is disclosed, herein horizontal rotation means rotation along the xy plane. Wherein, the magnetic direction of the magnetic capsule is in the xy plane and there are opposite magnetic dipole directions between the magnetic ball and the magnet inside the magnetic capsule.

In a tenth aspect of the present invention, a method to move the magnetic capsule vertically along the z direction is disclosed (FIGS. 27 and 28). Wherein, the magnetic direction of the magnetic capsule is placed perpendicular to the center dividing line. In one embodiment, moving the magnetic capsule up in a z direction is primarily by attracting the magnetic capsule upwardly by the upper magnetic ball, by the upper magnetic ball have the same magnetic direction as the magnetic capsule. Optionally, the lower magnetic ball is moved away to reduce its attraction to the magnetic capsule. Alternatively, or preferably, the lower magnetic ball further the lower magnetic ball further provides a repelling magnetic force by turning the magnetic direction opposite to that of the magnetic capsule. Similarly, moving the magnetic capsule downwardly can be accomplished by primarily attracting the magnetic capsule by the lower magnetic ball, provided that the magnetic direction of the lower magnetic ball is the same as that of the magnetic capsule. Optionally, the upper magnetic ball can be moved away to reduce its attraction to the magnetic capsule. Alternatively, or preferably, the upper magnetic ball can be further adjusted to provide a repelling magnetic force by turning the magnetic direction opposite to that of the magnetic capsule.

When the distance between the magnetic capsule and a first magnetic ball is three times more than the distance between the magnetic capsule and a first magnetic ball, then the first magnetic ball is a primary magnetic ball and a dominate magnetic ball whereas the second magnetic ball is a secondary magnetic ball and a surrender magnetic ball, the influence of the surrender magnetic ball to the magnetic capsule can be ignored. Therefore, when the magnetic capsule moved closer to the primary magnetic ball and its distance to a surrender magnetic ball is less than a third of the distance between the capsule and primary magnetic ball, then the surrender magnetic ball does not need to be adjusted in its position or orientation to repel the magnetic capsule.

The above-disclosed movements of the magnetic capsule are basic movement steps. A different combination of the basic movement steps will allow complicated movement sequence to occur in the target area.

One exemplar system that can be used to accomplish the basic and complicated movement sequences is listed in FIGS. 2-7.

In the scope of the present invention, xyz coordinate system is used to define a position or direction. FIG. 3 shows xyz axis direction with respect to the orientation of the medical system in the scope of the present invention. It is for illustration purposes only. It should not be construed as a limitation. For example, according to FIG. 3, in referring to FIG. 2, x direction is the direction the bed moves, which is from back to forward; y direction is the direction from one supporting frame to another opposing supporting frame, which is from left to right, and z direction is the direction to move the magnets closer and away to the patient, which is the up down direction. Horizontal rotation means a rotation around z axis, along xy plane, for example rotation from left to right, when viewing from the front of the apparatus. Vertical rotation means a rotation around y axis, along yz plane, for example, rotation from top to bottom, when viewing from the front of the apparatus.

ELEMENTS IN THE FIGURES ARE

Element 1. Motor 1
Element 2. Z-axis upper assembly 1
Element 3. Y-axis upper horizontal assembly
Element 4. Motor 3
Element 5. Magnetic ball 1
Element 6. Right supporting frame assembly
Element 7. Right sliding rail for the bed
Element 8. Magnetic ball 2
Element 9. Y-axis lower horizontal assembly
Element 10. Motor 8
Element 11. Z-axis uplift assembly 2
Element 12. Motor 6
Element 13. Base
Element 14. Motor 2
Element 15. Motor 4
Element 16. Motor 5
Element 17. Left supporting frame assembly
Element 18. Bed
Element 19. Left sliding rail for the bed
Element 20. Motor 9
Element 21. Motor 10
Element 22. Motor 7
Details of the elements and their functions are:
Element 1. Motor 1:
provide power to move the upper magnetic ball up in Z direction
Element 2. Z-axis upper assembly 1
movement control parts for the upper magnetic ball along Z-axis are all placed on Z-axis upper assembly
Element 3. Y-axis upper horizontal assembly
movement control parts for the upper magnetic ball along Y-axis are all placed on Y-axis upper assembly
Element 4. Motor 3
provide power to move the upper magnetic ball up in x direction
Element 5. Magnetic ball 1
the magnetic ball above the bed
Element 6. Right supporting frame assembly
supporting frame on the right and parts attached to it
Element 7. Right sliding rail for the bed
sliding rail for the bed on the right side
Element 8. Magnetic ball 2
the magnetic ball below the bed
Element 9. Y-axis lower horizontal assembly
movement control parts for the lower magnetic ball along Y-axis are all placed on Y-axis lower assembly
Element 10. Motor 8
provide power to move the lower magnetic ball in x direction
Element 11. Z-axis uplift assembly 2
movement control parts for the lower magnetic ball along z-axis are all placed on z-axis lower assembly
Element 12. Motor 6
provide power to move the lower magnetic ball in z direction
Element 13. Base
apparatus base, placed on the ground
Element 14. Motor 2
provide power to move the upper magnetic ball in y direction
Element 15. Motor 4
provide power to turn the upper magnetic ball along the horizontal plane, rotate around the z direction
Element 16. Motor 5
provide power to turn the upper magnetic ball along the vertical plane, rotate around the z direction
Element 17. Left supporting frame assembly
Left apparatus supporting frame
Element 18. Bed
Bed to provide support to a patient and carry the patient into/out of the examination area
Element 19. Left sliding rail for the bed
sliding rail for the bed on the left
Element 20. Motor 9
provide power to rotate the lower magnetic ball along the vertical plane, rotate around the z direction
Element 21. Motor 10
provide power to rotate the lower magnetic ball along the horizontal plane, rotate around the z direction
Element 22. Motor 7
provide power to move the lower magnetic ball in the y direction Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to affect such feature, structure, or characteristic in connection with other ones of the embodiments. Furthermore, for ease of understanding, certain method procedures may have been delineated as separate procedures; however, these separately delineated procedures should not be construed as necessarily order dependent in their performance. That is, some procedures may be able to be performed in an alternative ordering, simultaneously, etc. In addition, exemplary diagrams illustrate various methods in accordance with embodiments of the present disclosure. Such exemplary method embodiments are described herein using and can be applied to corresponding apparatus embodiments; however, the method embodiments are not intended to be limited thereby.

Although few embodiments of the present invention have been illustrated and described, it would be appreciated by those skilled in the art that changes may be made in these embodiments without departing from the principles and spirit of the invention. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein. As used in this disclosure, the term "preferably" is non-exclusive and means "preferably, but not limited to." Terms in the claims should be given their broadest interpretation consistent with the general inventive concept as set forth in this description. For example, the terms "coupled" and "connect" (and derivations thereof) are used to connote both direct and indirect connections/couplings. As another example, "having" and "including", derivatives thereof and similar transitional terms or phrases are used synonymously with "comprising" (i.e., all are considered "open ended" terms)—only the phrases "consisting of" and "consisting essentially of" should be considered as "close ended". Claims are not intended to be interpreted under 112 sixth paragraph unless the phrase "means for" and an associated function appear in a claim and the claim fails to recite sufficient structure to perform such function.

The invention claimed is:

1. A method to navigate a magnetic capsule, comprises
introducing the magnetic capsule into a target area, said magnetic capsule has a longitude direction and the magnetic dipole placed inside the magnetic capsule has a magnetization direction coincide with the longitude direction of the magnetic capsule;
placing the magnetic capsule in a first orientation, including its magnetic direction in a z direction;
providing an external magnetic control system comprising two magnetic balls, placed on opposing sides of the target area; and
rotating the magnetic capsule in the target area to adopt a second orientation while maintaining its position in xyz coordinates.

2. The method of claim 1, wherein the two magnetic balls are upper and lower magnetic balls.

3. The method of claim 2, wherein in the first orientation of the magnetic capsule, the two magnetic ball having a magnetic direction mirror to image to each other across a center dividing line between them, the magnetic directions of the two magnetic balls form an angle at 0-90 degrees between the center dividing line.

4. The method of claim 3, further comprising
turning the upper magnetic ball counter clockwise while maintaining its position; and
keeping the position and orientation of the bottom magnetic ball unchanged.

5. The method of claim 3, further comprising
turning both magnetic balls 0-360 degrees, simultaneously in a clockwise manner along xz plane.

6. The method of claim 2, wherein in the first orientation of the magnetic capsule, the two magnetic ball having a magnetic direction parallel to each other and point to the same direction.

7. The method of claim 6, wherein the second orientation differs in 0-90 degrees from the first orientation in a counter clock wise direction.

8. The method of claim 6, wherein the second orientation differs in 0-360 degrees from the first orientation in a clockwise direction.

* * * * *